US005773582A

United States Patent [19]
Shin et al.

[11] Patent Number: 5,773,582
[45] Date of Patent: Jun. 30, 1998

[54] TUMOR NECROSIS FACTOR MUTEINS

[75] Inventors: Hang-Cheol Shin, Kwangmyung; Nam-Kyu Shin, Seoul; Inkyung Lee, Incheon; Sungzong Kang, Seoul, all of Rep. of Korea

[73] Assignee: Hanil Synthetic Fiber Co., Ltd., Kyungsangnam-do, Rep. of Korea

[21] Appl. No.: 538,875

[22] Filed: Oct. 4, 1995

Related U.S. Application Data

[63] Continuation of Ser. No. 193,336, Feb. 8, 1994, abandoned.

[30] Foreign Application Priority Data

Feb. 9, 1993 [KR] Rep. of Korea ................... 1993-1751

[51] Int. Cl.$^6$ ........................... C07K 14/52; A61K 38/19
[52] U.S. Cl. ........................... 530/351; 424/85.1; 514/2; 514/8; 514/12; 930/140
[58] Field of Search .......................... 530/351; 930/140; 424/85.1

[56] References Cited

U.S. PATENT DOCUMENTS

| | | | |
|---|---|---|---|
| 4,677,063 | 6/1987 | Mark et al. | 930/144 |
| 4,677,064 | 6/1987 | Mark et al. | 930/144 |
| 4,879,226 | 11/1989 | Wallace et al. | 530/351 |
| 4,990,455 | 2/1991 | Yamagishi | 435/69.5 |
| 5,247,070 | 9/1993 | Yamada et al. | 930/144 |
| 5,262,309 | 11/1993 | Nakamura et al. | 530/351 |
| 5,288,852 | 2/1994 | Yamada et al. | 930/144 |

FOREIGN PATENT DOCUMENTS

| | | |
|---|---|---|
| 86 475 A2 | 8/1983 | European Pat. Off. . |
| 90 892 A1 | 10/1983 | European Pat. Off. . |
| 155 549 A2 | 9/1985 | European Pat. Off. . |
| 168 214 A2 | 1/1986 | European Pat. Off. . |
| 251 037 A2 | 1/1988 | European Pat. Off. . |
| 0437610 A1 | 7/1991 | European Pat. Off. . |
| 0563714 A2 | 10/1993 | European Pat. Off. . |
| 3843534 | 7/1990 | Germany . |
| 63 160 598 | 7/1988 | Japan . |
| 02 177 896 | 7/1990 | Japan . |
| WO 88/06625 A2 | 9/1988 | WIPO . |
| WO 90/07579 A1 | 7/1990 | WIPO . |

OTHER PUBLICATIONS

Haranaka et al., *Int. J. Cancer,* 34, 263–267 (1984).
Gatanaga et al., *J. Biol. Resp. Mod.,* 8, 278–286 (1989).
Noguchi et al., *J. Immunother.,* 10, 105–111 (1991).
Nakamura et al., *Int. J. Cancer,* 48, 744–748 (1991).
Ostade, X. V. et al., *Nature,* 361, 266–269 (1993).
Brouckaert, P. et al., *TNF: Molecular and Cellular Biology and Clinical Relevance,* 226–232 (1993).
Lienard, D. et al., *TNF: Molecular and Cellular Biology and Clinical Relevance,* 233–238 (1993).
Eggermont, A.M.M. et al., *TNF: Molecular and Cellular Biology and Clinical Relevance,* 239–243 (1993).
Taguchi, T. et al., *TNF: Structure–Function Relationship and Clinical Application,* 269–274 (1992).
Yoshida, J. et al., *J. Neurosurg.,* 77, 77–83 (1992).
Maruno, M. et al., *Surg. Neurol.,* 41, 482–485 (1994).
Yamasaki, T. et al., *Neurol. Med. Chir.,* 34, 216–220 (1994).
Galanos, G. et al., *TNF/Cachectin and Related Cytokines,* 114–127 (1988).
Rosenberg J Clin Oncol 10:180 1992.
Nakamura, et al., "A Novel Recombinant Tumor Necrosis Factor–Alpha Mutant with Increased Anti–Tumor Activity and Lower Toxicity," *Int. J. Cancer,* 48:744–748 (1991).
Yamagishi, et al., "Structure—activity analysis of human tumor necrosis factor," *Protein Engineering,* p. 372 (1989).
Kamijo, et al., "Induction of Differentiation of Human Monoblastic and Myeloblastic Leukemia Cell Lines by TNF Muteins," *Biochemical and Biophysical Research Communications,* 160 (2):820–827 (1989).
Van Ostade, et al., "Structure—activity studies of human tumour necrosis factors," *Protein Engineering,* 7(1):5–22 (1994).
Zhang et al 1992 J Biol Chem. 267:24069–24075.
Yamagishi et al 1990 Protein. Eng. 3:713–719.
Ito et al 1991 Biochimica Biophysica Acta 1096:245–252.
Masegi et al. 1993 Biotechnol. Lett. 15:1107–1110.
Ostade et al. 1991 EMBOJ 10:827–836.

*Primary Examiner*—Garnette D. Draper
*Attorney, Agent, or Firm*—Townsend and Townsend and Crew, LLP

[57] ABSTRACT

Muteins of human tumor necrosis factor (hTNF), a process for production thereof, and DNAs encoding these muteins are found to have a superior antitumor activity and lower acute lethal toxicity compared to the wild-type human tumor necrosis factor.

9 Claims, 2 Drawing Sheets

TUMOR NECROSIS FACTOR MUTEINS

This is a continuation of application No. 08/193,336, filed Feb. 8, 1994, now abandoned.

FIELD OF THE INVENTION

The present invention relates to human tumor necrosis factor muteins with superior anti-tumor activities, a process for the preparation thereof, and polynucleotides encoding said muteins.

BACKGROUND OF THE INVENTION

Tumor necrosis factor("TNF" or "TNF-α"), which is a cytokine produced primarily by activated monocytes and macrophages, is known to induce hemorrhagic necrosis of transplanted tumors *in vivo* and to be cytotoxic towards various tumor cell lines *in vitro* [Aggarwal, B.B., *Drugs of the Future*, 891–898(1987)). TNF is also known to show antiviral activities [Mestan, J. et al., *Nature*, 323, 816–819 (1986); Wong, G.H.W. & Goeddel, D.V., *Nature*, 323, 819–822 (1986)] and to deactivate certain species of malarial parasites in vivo [Taverne, J. et al., *Clin. Exp. Immunol.*, 67, 1(1987)].

TNF is initially produced as a prohormone; however, when it is secreted, 76-amino acid residues are cleaved off from its amino terminal region to form an active mature human TNF having one intramolecular disulfide bond [Aggarwal, B.B. et al., *J. Biol. Chem.*, 260, 2345–2354 (1985)].

The gene coding human tumor necrosis factor was cloned and expressed in *Escherichia coli* in 1984 [Pennica, D. et al., *Nature*, 312, 724–729(84); Shirai, T. et al., *Nature*, 313, 803–806(1985)].

However, wild-type TNF failed to produce a satisfactory anti-cancer effect for the treatment of cancer patients when it was administered alone, particularly when it was used for systemic therapy [Blick, M. et al., *Cancer Res.*, 47, 2986 (1987); Creaven, P.J. et al., *Cancer Chemother. Pharmacol.*, 20, 137(1987); Kimura, K. et al., *Cancer Chemother. Pharmacol.*, 20, 223(1987)]. The reason for the failure resides in the fact that TNF is highly toxic and causes serious side effects and, therefore, cannot be administered in a sufficient dosage to exhibit the anti-cancer effect.

To overcome this problem, various attempts have been made to produce TNF muteins with a higher anti-tumor activity but reduced side effects, for example, by way of removing several amino acids at the amino terminus and/or inducing a random mutagenesis(Mattews et al., *Br. J. Cancer*, 42, 416 (1980); Ruff et al., *J. Immunol.*, 125, 1671(1980); Mannel et al., *Infect. Immunity*, 28, 204 (1980); Haranaka et al., *Japan. J. Exp. Med.*, 51, 191(1981); European Patent Publication No. 908092; European Patent Publication No. 86475; Japanese Patent Publication No. 21621/1983; European Patent Publication No. 155 549(1985); European Patent Publication No. 168 214(1985); and European Patent Publication No. 251 037(1987)). However, the results obtained from such TNF muteins show at best a 7-fold higher anti-tumor activity than that of the wild-type TNF[Nakamura, S. et al., *Int. J. Cancer*, 48, 744–748 (1991)].

On the other hand, the three-dimensional structure of human TNF ("hTNF") is known to be in the form of an elongated, antiparallel β-pleated sheet sandwich structure with a "jelly-roll" topology and to exist as a trimer with 3-fold axis of symmetry[Jones, E.Y. et al., *Nature(London)*, 338, 225–228(1989); Eck, M.J. and Sprang, S.R., *J. Biol. Chem.*, 264, 17595–17605(1989)]. The determination of the three-dimensional structure of hTNF by X-ray crystallography[Eck, M.J. and Sprang, S.R., *J. Biol. Chem.*, 264, 17595–17606(1989)] and mutational analyses [Ostade, X.V., *EMBO J.*, 10, 827–836 (1991)] has suggested that the active site(s) of TNF for anti-tumor activity may be located at the polypeptide regions around each side of the three grooves which are formed by the three monomers gathered in the base of the three-dimensional structure.

Unexpectedly, the present inventors have succeeded in developing certain TNF muteins having a higher anti-tumor activity than that of the wild-type TNF or any known TNF muteins by way of a systemic mutagenesis of said polypeptide regions. More specifically, at least one of the amino acids in the six polypeptide regions at the base of the TNF trimer molecule, namely, N-terminal region or region l(the 1st to the 10th amino acids), region 2(the 37th to the 41st amino acids), region 3(the 52nd to the 56th amino acids), region 4(the 84th to the 88th amino acids), region 5(the 126th to the 130th amino acids), and region 6(the 156th to the 157th amino acids) is mutagenized into hydrophobic, positively charged or negatively charged residues.

SUMMARY OF THE INVENTION

Accordingly, it is an object of the present invention to provide a TNF mutein having an excellent anti-tumor activity wherein at least one of the amino acids in the six polypeptide regions at the base of the TNF trimer molecule is replaced by another amino acid.

It is another object of the present invention to provide a polynucleotide encoding the TNF mutein.

It is a further object of the present invention to provide a vector comprising said polynucleotide and a host cell transformed with the vector.

It is a still another object of the present invention to provide a process for producing the TNF mutein by employing the transformant.

It is a still further object of the present invention to provide a pharmaceutical composition comprising the TNF mutein as an active ingredient.

In accordance with one aspect of the present invention, there is provided a TNF mutein wherein at least one of the 4th to the 10th, the 38th to the 41st, the 52nd to the 54th, the 56th, the 85th to the 88th, the 127th to the 129th, the 156th and the 157th amino acids of the wild type TNF polypeptide comprising the following amino acid sequence[1](SEQ ID NO:1) is replaced by another amino acid, with or without deleting one or more of the 1st to the 7th amino acids from the N-terminus:

|     |     |     |     |     |     |     |     |     |     |     |
| --- | --- | --- | --- | --- | --- | --- | --- | --- | --- | --- |
|     | Val | Arg | Ser | Ser | Ser | Arg | Thr | Pro | Ser | Asp | Lys[1] |
| Pro | Val | Ala | His | Val | Val | Ala | Asn | Pro | Gln | Ala | Glu |
| Gly | Gln | Leu | Gln | Trp | Leu | Asn | Arg | Arg | Ala | Asn | Ala |
| Leu | Leu | Ala | Asn | Gly | Val | Glu | Leu | Arg | Asp | Asn | Gln |
| Leu | Val | Val | Pro | Ser | Glu | Gly | Leu | Tyr | Leu | Ile | Tyr |
| Ser | Gln | Val | Leu | Phe | Lys | Gly | Gln | Gly | Cys | Pro | Ser |
| Thr | His | Val | Leu | Leu | Thr | His | Thr | Ile | Ser | Arg | Ile |
| Ala | Val | Ser | Tyr | Gln | Thr | Lys | Val | Asn | Leu | Leu | Ser |
| Ala | Ile | Lys | Ser | Pro | Cys | Gln | Arg | Glu | Thr | Pro | Glu |
| Gly | Ala | Glu | Ala | Lys | Pro | Trp | Tyr | Glu | Pro | Ile | Tyr |
| Leu | Gly | Gly | Val | Phe | Gln | Leu | Glu | Lys | Gly | Asp | Arg |
| Leu | Ser | Ala | Glu | Ile | Asn | Arg | Pro | Asp | Tyr | Leu | Asp |
| Phe | Ala | Glu | Ser | Gly | Gln | Val | Tyr | Phe | Gly | Ile | Ile |
| Ala | Leu |     |     |     |     |     |     |     |     |     |     |

BRIEF DESCRIPTION OF THE DRAWINGS

The above objects and features of the present invention will become apparent from the following description of preferred embodiments given in conjuction with the accompanying drawings, in which.

DETAILED DESCRIPTION OF THE PREFERRED EMBODIMENT

Figure 1:
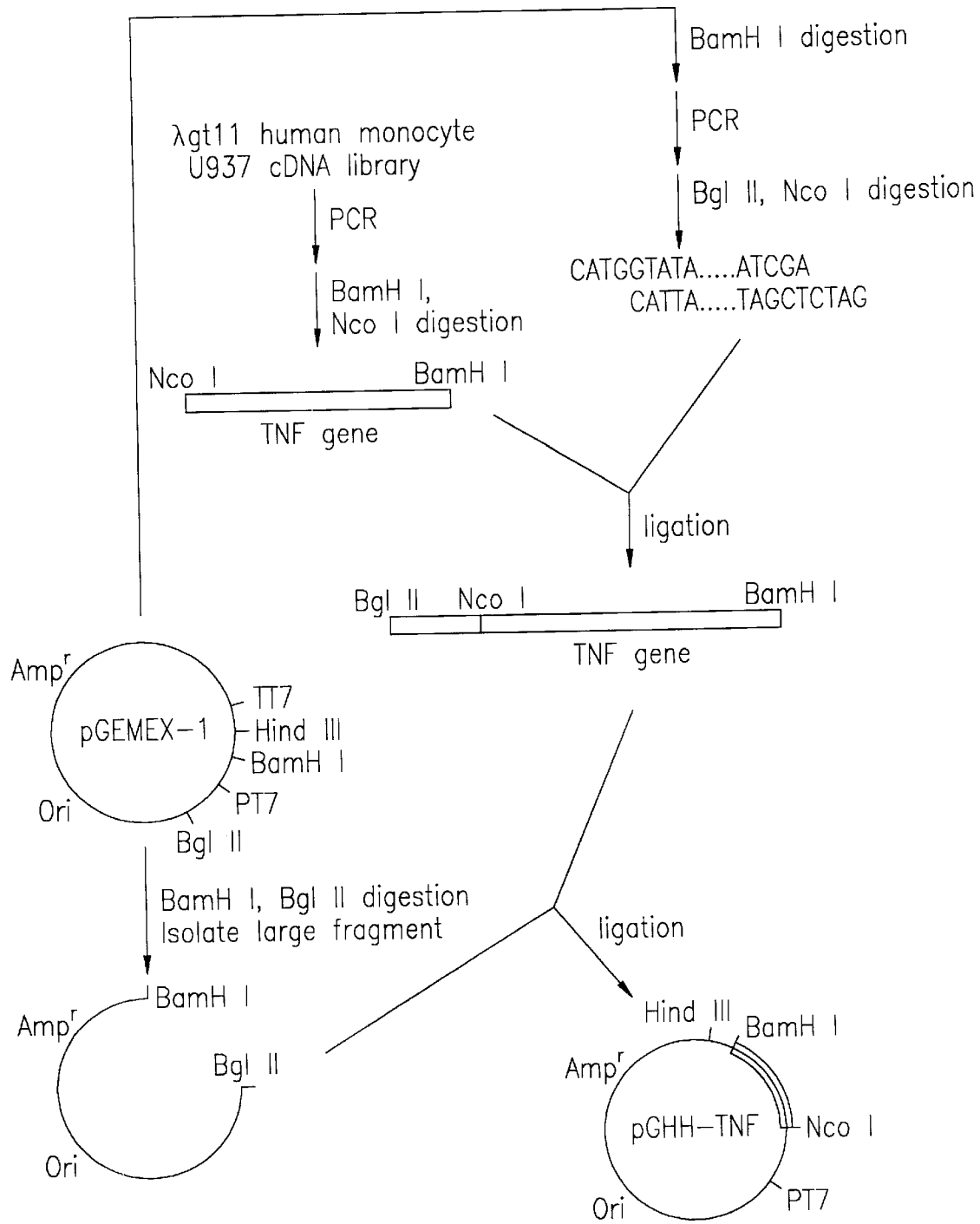
FIG. 1 shows a scheme for constructing a plasmid PGHH-TNF.

A TNF mutein of the present invention has an amino acid sequence wherein at least one of the following amino acid replacements occurs in the amino acid sequenced]:

Replacements of

4th Serine by Arginine;

5th Serine by Arginine;

6th Arginine by Alanine;

7th Threonine by Histidine or Lysine;

8th Proline by Arginine;

9th Serine by Lysine;

10th Aspartic acid by Arginine;

38th Alanine by Aspartic acid;

39th Asparagine by Aspartic acid, Lysine or Valine;

40th Glycine by Aspartic acid, Lysine or Valine;

41st Valine by Serine;

52nd Serine by Isoleucine, Glutamic acid or Lysine;

53rd Glutamic acid by Lysine or Leucine;

54th Glysine by Aspartic acid or Valine;

56th Tyrosine by Phenylalanine or Glutamic acid;

85th Valine by Glutamic acid or Arginine;

86th Serine by Leucine, Lysine, Glutamic acid or Aspartic acid;

87th Tyrosine by Glutamic acid or Arginine;

88th Glutamine by Glutamic acid;

127th Glutamic acid by Alanine, Valine or Lysine;

128th Lysine by Alanine, Valine or Glutamic acid;

129th Glycine by Glutamic acid, Lysine or Valine;

156th Alanine by Aspartic acid; and

157th Leucine by Phenylalanine, optionally deleting one or more of the 1st to the 7th amino acids, preferably 3 to 7 among the above seven amino acids from the N-terminus in the amino acid sequence of the mutein.

Further, when the TNF mutein is produced in a microorganism such as E. coli, it will have Met attached to the N-terminus of the above amino acid sequence since ATG encoding Met, which is essential for initiating the translation, is necessarily included in the process.

For the expression of the polynucleotide of the present invention in a microorganism such as E. coli, ATG initiation codon is necessary; and it may be provided by a vector wherein which the polynucleotide is inserted, or may be added in the polynucleotide sequence of the present invention.

The polynucleotide encoding a human TNF mutein of the present invention may be produced by chemically synthesizing the total sequence; or by chemically synthesizing an oligonucleotide containing the region to be replaced and then amplifying it through a polymerase chain reaction ("PCR")[Saiki, R.K. et al., Science, 230, 1350–1354(1985)] using a human TNF cDNA comprising, for example, the following polynucleotide sequence [2](SEQ ID NO:2) as a template and the oligonucleotide as a primer:

```
(5')  GTC  AGA  TCA  TCT  TCT  CGA  ACC  CCG  AGT  [2]
GAC  AAG  CCT  GTA  GCC  CAT  GTT  GTA  GCA  AAC
CCT  CAA  GCT  GAG  GGG  CAG  CTC  CAG  TGG  CTG
AAC  CGC  CGG  GCC  AAT  GCC  CTC  CTG  GCC  AAT
GGC  GTG  GAG  CTG  AGA  GAT  AAC  CAG  CTG  GTG
GTG  CCA  TCA  GAG  GGC  CTG  TAC  CTC  ATC  TAC
TCC  CAG  GTC  CTC  TTC  AAG  GGC  CAA  GGC  TGC
CCC  TCC  ACC  CAT  GTG  CTC  CTC  ACC  CAC  ACC
ATC  AGC  CGC  ATC  GCC  GTG  TCC  TAC  CAG  ACC
AAG  GTC  AAC  CTC  CTC  TCT  GCC  ATC  AAG  AGC
CCC  TGC  CAG  AGG  GAG  ACC  CCA  GAG  GGG  GCT
GAG  GCC  AAG  CCC  TGG  TAT  GAG  CCC  ATC  TAT
CTG  GGA  GGG  GTC  TTC  CAG  CTG  GAG  AAG  GGT
GAC  CGA  CTC  AGC  GCT  GAG  ATC  AAT  CGG  CCC
GAC  TAT  CTC  GAC  TTT  GCC  GAG  TCT  GGG  CAG
GTC  TAC  TTT  GGG  ATC  ATT  GCC  CTG  (3')
```

For example, DNA encoding a TNF mutein, in which the 4th and the 5th amino acids (serines) are replaced by arginines and three amino acids are deleted from the N-terminus thereof, can be produced in accordance with the following procedures.

A DNA fragment having a nucleotide sequence encoding the wild type hTNF-α is prepared by using a PCR method from the U937 human monocyte cDNA library (Clontech, USA). A sense primer with a restriction site at the 5' end and a modified nucleotide sequence and an anti-sense primer with a restriction site at the 5' end are chemically synthesized; and, thereafter, PCR is carried out by using the DNA encoding the wild type TNF-α as a template and the primers to prepare the DNA encoding the TNF mutein.

The hTNF mutein of the present invention can be produced by inserting the modified DNA obtained as above into an expression vector after digesting it with restriction endonucleases providing restriction sites at both ends thereof, transforming a host cell with the resulting vector and culturing the transformant under a condition which allows the expression of the modified DNA fragment.

More specifically, an expression vector system for the production of the TNF mutein of the present invention can be produced by preparing a DNA fragment encoding the TNF mutein which also has a translation initiation codon, ATG, at the 5'-end and a termination codon at the 3'-end, ligating to the DNA fragment a suitable promoter(e.g., lac, trp, tac, PL, T3, SP6, T7, SV40, λ(pL/pR), and the like) and a ribosome binding site, and then inserting the resulting fragment into a vector, e.g., a plasmid(e.g., pBR322), a phage(e.g., a lambda phage derivative) DNAs, and a virus (e.g., SV40) DNAs.

The transformant can be obtained by transforming a suitable host, for example, E. coli, with the resulting expression vector in accordance with the method of, e.g., Cohen et al. [Cohen, et al., Proc. Natl. Acad. Sci. USA, 69, 2110(1972)].

Then the transformant is cultured under a suitable condition to express the modified polynucleotide coding the desired TNF mutein. The cultured cells are treated by, for example, lysozyme digestion, freezing-thawing, ultrasonication or French press, and then centrifuged or filtered to obtain an extract containing the desired mutein.

The desired mutein can be isolated from the extract through a conventional purification process such as ultrafiltration, dialysis, ion exchange chromatography, gel filtration, electrophoresis, affinity chromatography and the like. The concentration of the purified TNF mutein may be measured in accordance with, e.g., Bradford's method [Bradford, M., Anal. Biochem. 72, 248(1976)].

The in vitro anti-tumor activity may be determined as a direct cell-killing activity(cytotoxicity) using a TNF-sensitive murine fibrosarcoma L-929 cell line (ATCC CCL1) [Ruff, M.R. & Gifford, G.E.: Lymphokines, (ed. Edgar Pick) 2, 235(1981), Academic Press, New York] as follows:

3 to 4×104 cells (150µl) per well of L-929 cells are seeded into a 96-well microtiter plate containing Dulbecco's modified medium with 2% fetal calf serum. The microplate is well-shaken and then incubated at 37° C. in a thermostat containing 5% $CO_2$. After 24 hrs, the medium is removed and a new medium containing 2µg/ml of actinomycin D is added to the microplate in an amount of 100 µl per well. Each of the TNF samples which are prepared by two-fold diluting serially is treated with ultraviolet rays for 30 minutes and placed onto a microtiter plate containing L929 cells in an amount of 100 µl per well. The cells are further incubated at 37° C. in a thermostat containing 5% $CO_2$ for 18hrs, and then stained for 15–20 mins with a crystal violet solution comprising crystal violet 0.5 g/l, ethanol 112 ml/l, formaline 101 ml/l (saturated with $CaCO_3$) and distilled water 786 ml/l . The microtiter plate is washed thoroughly with tap water and dried. The absorbance of the microtiter plate is measured at 540 nm using Molecular Devices microplate reader.

Cytotoxicity of each mutein is calculated from the absorbance(Abs.) as follows:

$$\text{Cytotoxicity}(\%) = \frac{(\text{Abs.}) \text{ of the control* at } 540 \text{ nm-Abs. of the sample at } 540 \text{ nm}}{\text{Abs. of the control * at } 540 \text{ nm}} \times 100$$

-continued

*As a control, the L-929 cells not treated with any TNF are used.

One unit is defined as the amount of TNF required for 50% cell killing.

Tumor necrosis factor or tumor necrosis factor muteins of the present invention can be formulated, for administration, into a unit dose or multi-dose form in accordance with a known method, e.g., by mixing with physiologically acceptable carriers, i.e., water, buffers, Ringer's solution, dextrose solution or 5% human serum albumin. The formulation may further contain antioxidants such as ascorbic acid, low molecular weight polypeptides, proteins, amino acids or carbohydrates such as glucose or dextrin.

The pharmaceutical composition can be administered intravenously, intraperitoneally, intramuscularly or intralesionally, i.e., by a direct injection into solid tumors. If desired, TNF or TNF muteins may be administered in combination with other antineoplastic agents such as cysplatin, actinomycin-D, adriamycin, etc.; the immune modulators such as immunoglobulins, e.g., gamma globulin; or interferons. A typical formulation comprises TNF and gamma interferon in such an amount that the unit activity ratio of TNF: interferon ranges from 0.1:1 to 200:1. The dosage level of TNF or TNF mutein is preferably in a range from 5 to 20 µg/kg/day which may be varied depending on the routes and frequency of administration, and the condition of a subject patient.

The following Examples are intended to specifically exemplify the present invention without limiting the scope of the present invention.

EXAMPLE 1: Production of human TNF polypeptide 1-A.
Construction of a plasmid containing human TNF cDNA Step 1. Construction of a pGHH-TNF plasmid A DNA fragment comprising a nucleotide sequence [2] encoding human wild type TNF-α was prepared by carrying out PCR using as a template human monocyte cDNA library (Clontech) prepared from the U937 cell. The nucleotide sequence of the used primers are as follows:
Sense primer(SEQ ID NO:3):
  5'-GCACCATGGTCAGATCATCTTCTCGAACC-3'
Anti-sense primer(SEQ ID NO: 4):
  3,-TGAAACCCTAGTAACGGGACACTATTCCTAGG TGT-5'

The prepared PCR products were digested with the restriction endonucleases NcoI and BamHI to prepare a double strand DNA("fragment 1") with cohesive ends. pGEMEX-1 (Promega) with T7 expression system was used as an expression vector system, which was modified to have NcoI site instead of NdeI restriction site in order to inhibit the TNF gene from being expressed as a fusion protein containing T7 gene 10 protein; and was digested with a restriction endonuclease BamHI. The resultant linear plasmid was digested with a restriction endonuclease BglII.

Meanwhile, the following PCR product containing T7 promoter and the restriction endonuclease sites NcoI at 5'-end and BglII at 3'-end(SEQ ID NO: 5) was prepared by carrying out PCR using the linear plasmid prepared by BamHI digestion as a template. The underlined nucleotide sequence indicates T7 promoter region.

5'-GCACCATGGTATATCTCCTTCTTAAAGTTAAACAAAATTATTTCTAGAGGGAAACCT
TTGTGGTCTCCCTATAGTGAGTCGTATTAATTTCGCGGGATCGAGATCTCCC-3'

The following primers were used to prepare the above PCR product:
Sense primer(SEQ ID NO: 6):
  5'-GCACCATGGTATATCTCCTTCTTAAAG-3'
Anti-sense primer(SEQ ID NO: 7):
  3'-AAAGCGCCCTAGCTCTAGAGGG-5'

After the PCR product was digested with the restriction endonucleases BglII and NcoI, the resultant fragment was ligated to the fragment 1 containing TNF gene by using T4 DNA ligase . Then the combined DNA fragment was inserted into a vector pGEMEX-1 digested with the restriction endonucleases BamHI and BglII to prepare an expression plasmid PGHH-TNF.
The procedure is depicted in FIG. 1.

Step 2. Construction of a pT7-TNF plasmid

A DNA fragment comprising a nucleotide sequence [2] encoding human wild type TNF-α is prepared by carrying out PCR using human monocyte cDNA library(Clontech) prepared from the U937 cell as a template. The nucleotide sequence of the used primers are as follows:
Sense primer(SEQ ID NO: 8):
  5'-GCCATACATATGGTCAGATCATCTTCTCGAACC-3'
Anti-sense primer(SEQ ID NO: 4):
  3'-TGAAACCCTAGTAACGGGACACTATTCCTAGG TGT-5'

The resultant PCR product was digested with the restriction endonucleases NdeI and BamHI to have NdeI restriction site at 5'end and BamHI restriction site at 3'-end ("fragment 2"). pT7–7 vector [Stanley Tabor & Charles C. Richardson, Proc. Natl. Acad. Sci. U.S.A., 82, 1074–1078 (1985); received from Department of Biological Chemistry, Harvard Medical School] was used as an expression vector system; and was digested with the restriction endonucleases BamHI and NdeI. Then, the DNA fragment containing TNF gene was inserted into the above prepared vector by using T4 DNA ligase to prepare an expression plasmid pT7-TNF.

Figure 2:
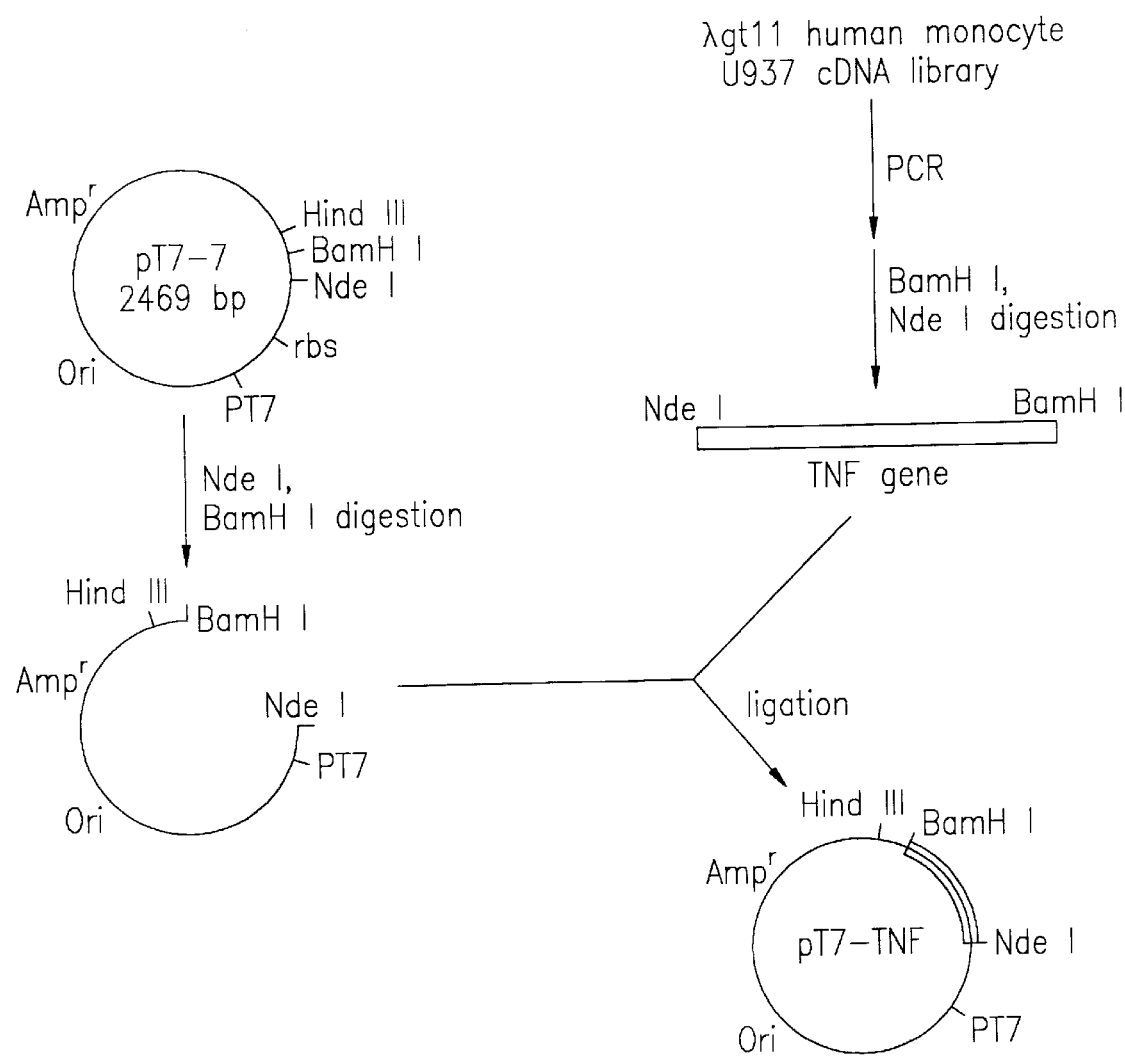
FIG. 2 depicts a scheme for constructing a plasmid pT7-TNF.

The procedure is depicted in FIG. 2.

1-B. Expression of human TNF

E. coli JM109 was transformed with each of the expression plasmids PGHH-TNF and pT7-TNF by the method described by Hanahan [Hanahan, D., DNA Cloning 1 (Ed. D.M. Glover), 109–135(1985), IRS Press]. Thereafter, ampicillin-resistent colony on LB/ampicillin agar plate (containing 50 $\mu$g/ml ampicillin) was selected and seeded to 1 ml of LB medium containing ampicillin, respectively. After each of the cultures was incubated at 37° C. overnight, it was centrifuged at 8000 xg for 2 mins to obtain the cells. The plasmid was isolated and purified from the E. coli pellet using alkaline lysis method. After the plasmid was dissolved in 50 $\mu$l of TE buffer(10 mM Tris-Cl, pH 8.0, 1 mM EDTA), 0.1 $\mu$g of plasmid solution was mixed with 2 $\mu$l of 10×Onephor-all buffer (100 mM Tris acetate, 100 mM magnesium acetate, and 500 mM potassium acetate), 1 unit of NcoI and 5 units of BamHI (in the case of pGHH-TNF plasmid) or 1 unit of NdeI and 5 units of BamHI (in the case of pT7-TNF plasmid), and distilled water was added thereto to make a final volume of 10 $\mu$l. The solution was incubated at 37° C. for 2 hours and subjected to 1% agarose gel electrophoresis to confirm that the desired DNA fragment was inserted into the plasmid. An expression host E. coli JM109 (DE3) was transformed with the plasmid which contains the desired insert by the same method as mentioned above and then, ampicillin-resistant colony was selected.

The E. coli JM109 (DE3) transformed with pGHH-TNF and pT7-TNF, respectively, were deposited to Korean Culture Center of Microorganisms (KCCM) in Jan. 28, 1993 (E. coli JM109 (DE3+ pGHH-TNF): accession number of KCCM-10021; E. coli JM109 (DE3+ pT7-TNF): accession number of KCCM-10020).

1-C. Purification of human TNF

The transformants obtained in (1-B) above containing pGHH-TNF and pT7-TNF plasmids, respectively, were seeded into 1 ml of LB medium and cultivated at 37° C. overnight. The culture was inoculated in 50 ml of LB medium containing ampicillin; and then IPTG (isopropyl thiogalactopyranoside) was added in a final concentration of 1 mM when the absorbance of the culture reached 0.1 to 0.4 at 600 nm. After the culture was shaking-incubated at 200 rpm for 4 hours, it was centrifuged at 8000xg for 2 mins to obtain E. coli pellets. The cells were suspended in 5 ml of 10mM sodium phosphate buffer (pH 7.4), and the suspension was subjected to ultrasonication to disrupt the cells.

The supernatant was separated by centrifugation of the disrupted cell solution at 15000xg and 4° C. for 30 mins and subjected to the quantification for the amount of total proteins using Bradford's method. And, then the supernatant was diluted to make a protein concentration of 10 mg/ml and then purified using Pharmacia FPLC system and mono-Q ion exchange column. The desired polypeptide was eluted with a linear concentration gradient of 0 M to 0.5 M NaCl in 10 mM sodium phosphate buffer (pH 7.4) and the fractions containing polypeptide having a molecular weight of about 17kd were collected and pooled. Each amount of TNF obtained was about 0.7 to 0.8 mg with more than 95% purity.

EXAMPLE 2 : Production of human TNF muteins

2-A. Construction of a plasmid containing human TNF mutein cDNA

Step 1. Construction of a PGHH-TNF mutein plasmid pGHH-TNF plasmid was digested with the restriction endonuclease NcoI and the resultant linear plasmid was digested with the restriction endonuclease HindIII and isolated the DNA fragment encoding TNF("TNF DNA1"). A DNA fragment comprising a nucleotide sequence encoding TNFR2-1 mutein was prepared as follows.

A series of PCR were carried out using the TNF DNA1 as a template and the mutant primers containing the nucleotide sequences to be mutated and P1 primers. The mutant primers are as follows:

R2-1: sense primer(SEQ ID NO: 9):
5'-AATGCCCTCCTGGCCGATGACGTGGAGCTGA GA-3' anti-sense primer(SEQ ID NO: 10):
3'-TTACGGGAGGACCGGCTACTGCACCTCGACT CT-5'

Further, the P1 primers which are complementary to the 5'-end and the 3'-end of TNF DNA1, respectively, are also used.

P1: Sense primer(SEQ ID NO:3):
5'-GCACCATGGTCAGATCATCTTCTCGAACC-3'
Anti-sense primer(SEQ ID NO: 11):
3'-CCCTAGTAACGGGACACTATTTTCGAATGT-5'

First, PCR was carried out by employing R2-1 sense primer and P1 anti-sense primer and the TNF DNA1 as a template; second PCR was carried out by employing R2-1 anti-sense primer and P1 sense primer and the TNF DNA1; and the PCR products were combined and annealed.

Then, TNFR2-1 mutein DNA having the restriction endonuclease sites of NcoI at 5' end and HindIII at 3' end was amplified by carrying out PCR using the primers (P1).

The resultant PCR product was digested with the restriction endonucleases NcoI and HindIII to prepare a DNA fragment with the restriction sites at each end. Then, the TNFR2-1 mutein DNA fragment was ligated to the linear plasmid with the restriction sites of NcoI and HindIII prepared by digesting the plasmid PGHH-TNF with NcoI and HindIII endonucleases by using T4 DNA ligase to prepare the plasmid pGHH-TNFR2-1.

Plasmids containing the DNA fragments encoding other TNF muteins were also prepared by the same procedure as mentioned above, except that R2-1 primers were substituted with the following primers. P1 primers were used to amplify all the mutein DNAs.

R2-2:sense primer(SEQ ID NO: 12):
5'-CTCCTGGCCAAGAAAGTGGAGCTGAGA-3' anti-sense primer(SEQ ID NO: 13):
3'-GAGGACCGGTTCTTTCACCTCGACTCT-5'
R2-3:sense primer(SEQ ID NO: 14):
5'-CTCCTGGCCGTTGTAGTGGAGCTGAGA-3' anti-sense primer(SEQ ID NO: 15):
3'-GAGGACCGGCAACATCACCTCGACTCT-5'
R2-4:sense primer(SEQ ID NO: 16):
5'-AATGCCCTCCTGGACAATGGCGTG-3' anti-sense primer(SEQ ID NO 17):
3'-TTACGGGAGGACCTGTTACCGCAC-5'
R2-5:sense primer(SEQ ID NO: 18):
5'-AATGCCCTCCTGGACAATGGCTCCGAGCTGA GA-3' anti-sense primer(SEQ ID NO: 19):
3'-TTACGGGAGGACCTGTTACCGAGGCTCGACT CT-5'
R3-1:sense primer(SEQ ID NO: 20):
5'-TCAGAGGGCCTGTTCCTCATCTAC-3' anti-sense primer(SEQ. ID NO: 21):
3'-AGTCTCCCGGACAAGGAGTAGATG-5'
R3-2:sense primer(SEQ ID NO: 22):
5'-TGGTGCCAATAGAGGGCCTGTACCT-3' anti-sense primer(SEQ ID NO 23):
3'-ACCACGGTTATCTCCCGGACATGGA-5'
R3-3:sense primer(SEQ ID NO: 24):
5'-TGGTGCCAGAAGAGGGCCTGTACCT-3' anti-sense primer(SEQ ID NO: 25):
3'-ACCACGGTCTTCTCCCGGACATGGA-5'

R3-4: sense primer(SEQ ID NO: 26):
5'-TGGTGGTGCCAAAAAAGGGCCTGTAC-3' anti-sense primer(SEQ ID NO: 27):
3'-ACCACCACGGTTTTTTCCCGGACATG-5'
R3-5: sense primer(SEQ ID NO: 28):
5'-TGGTGCCATCACTGGGCCTGTTC-3' anti-sense primer(SEQ ID NO: 29):
3'-ACCACGGTAGTGACCCGGACAAG-5'
R3-6: sense primer(SEQ ID NO: 30):
5'-CCATCAGAGGACCTGTACCTC-3' anti-sense primer(SEQ ID NO: 31):
3'-GGTAGTCTCCTGGACATGGAG-5'
R3-7: sense primer(SEQ ID NO: 32):
5'-CCATCAGAGGTCCTGTACCTC-3' anti-sense primer(SEQ ID NO: 33):
3'-GGTAGTCTCCAGGACATGGAG-5'
R3-8: sense primer(SEQ ID NO: 34):
5'-TCAGAGGGCCTGGAACTCATCTAC-3' anti-sense primer(SEQ ID NO: 35):
3'-AGTCTCCCGGACCTTGAGTAGATG-5'
R4-1: sense primer(SEQ ID NO: 36):
5'-ATCGCCGTCTTGTACCAGACCAAG-3' anti-sense primer(SEQ ID NO: 37):
3'-TAGCGGCAGAACATGGTCTGGTTC-5'
R4-2: sense primer(SEQ ID NO: 38):
5'-CGCATCGCCGAGAAAGAACAGACCAAG-3' anti-sense primer(SEQ ID NO: 39):
3'-GCGTAGCGGCTCTTTCTTGTCTGGTTC-5'
R4-3: sense primer(SEQ ID NO: 40):
5'-ATCGCCGTCAAATACCAGACCAAG-3' anti-sense primer(SEQ ID NO: 41):
3'-TAGCGGCAGTTTATGGTCTGGTTC-5'
R4-4: sense primer(SEQ ID NO: 42):
5'-ATCGCCGTCTCCAACAGACCAAG-3' anti-sense primer(SEQ ID NO: 43):
3'-TAGCGGCAGAGGCTTGTCTGGTTC-5'
R4-5: sense primer(SEQ ID NO: 44):
5'-ATCGCCGTCGAGTACGAGACCAAGGTC-3' anti-sense primer(SEQ ID NO: 45):
3'-TAGCGGCAGCTCATGCTCTGGTTCCAG-5'
R5-1: sense primer(SEQ ID NO: 46):
5'-TCCAGCTGGCTGCTGGTGACCGA-3' anti-sense primer(SEQ ID NO: 47):
3'-AGGTCGACCGACGACCACTGGCT-5'
R5-2: sense primer(SEQ ID NO: 48):
5'-TCCAGCTGGTTGTTGGTGACCGA-3' anti-sense primer(SEQ ID NO: 49):
3'-AGGTCGACCAACAACCACTGGCT-5'
R5-3: sense primer(SEQ ID NO: 50):
5'-TTCCAGCTGAAGAAGGGTGACCGA-3' anti-sense primer(SEQ ID NO: 51):
3'-AAGGTCGACTTCTTCCCACTGGCT-5'
R5-4: sense primer(SEQ ID NO: 52):
5'-AGCTGGAGGAGGGTGACCGACT-3' anti-sense primer(SEQ ID NO: 53):
3'-TCGACCTCCTCCCACTGGCTGA-5'
R5-5: sense primer(SEQ ID NO: 54):
5'-AGCTGGAGAAGGAAGACCGACT-3' anti-sense primer(SEQ ID NO: 55):
3'-TCGACCTCTTCCTTCTGGCTGA-5'
R5-6: sense primer(SEQ ID NO: 56):
5'-AGCTGGAGAAGAAGGACCGACT-3' anti-sense primer(SEQ ID NO: 57):
3'-TCGACCTCTTCTTCCTGGCTGA-5'
R5-7: sense primer(SEQ ID NO: 58):
5'-AGCTGGAGAAGGTCGACCGACT-3' anti-sense primer(SEQ ID NO: 59):
3'-TCGACCTCTTCCAGCTGGCTGA-5'

Step 2. Construction of a pT7-TNF mutein plasmid

Construction of mutein plasmids DT7-TNFR1-1 to R1-6 pT7-TNF plasmid was digested with the restriction endonuclease NdeI and the resultant linear plasmid was digested with the restriction endonuclease HindIII and isolated the DNA fragment encoding TNF("TNF DNA2"). A DNA fragment comprising a nucleotide sequence encoding TNFR1-1 mutein was prepared by carrying out PCR using the TNF DNA2 as a template and mutant primers containing the nucleotide sequences to be mutated. The mutant primers are as follows:
R1-1: sense primer(SEQ ID NO: 60):
5'-TATCATATGCGTCGAACCCCGAGTGACAAG-3' anti-sense primer(SEQ ID NO: 11):
3'-CCCTAGTAACGGGACACTATTTTCGAATGT-5'

The resultant PCR product was digested with the restriction endonucleases NdeI and HindIII to prepare a DNA fragment with restriction sites at each end. Then, the TNFR1-1 mutein DNA fragment was ligated to the linear pT7-TNF plasmid which was prepared by digesting with the restriction endonucleases of NdeI and HindIII by using T4 DNA ligase.

By the same procedure as mentioned above, plasmids containing the DNA fragments encoding other TNFR1 muteins were also prepared. The used primers are as follows.
R1-2: sense primer(SEQ ID NO: 61):
5'-TATCATATGGCTCATCCGAGTGACAAGCCTG-3' anti-sense primer(SEQ ID NO: 11):
3'-CCCTAGTAACGGGACACTATTTTCGAATGT-5'
R1-3: sense primer(SEQ ID NO: 62):
5'-TATCATATGGCTCACCGGAAACGCAAGCCTGTA-3' anti-sense primer(SEQ ID NO: 11):
3'CCCTAGTAACGGGACACTATTTTCGAATGT-5'
R1-4: sense primer(SEQ ID NO: 63):
5'-CGCCATATGCGAAAACCGAGTGACAAGCC-3' anti-sense primer(SEQ ID NO: 11):
3'-CCCTAGTAACGGGACACTATTTTCGAATGT-5'
R1-5: sense primer(SEQ ID NO: 64):
5'-TATCATATGCGTCGTCGAACCCCGAGTGACAA-3' anti-sense primer(SEQ ID NO: 11):
3'-CCCTAGTAACGGGACACTATTTTCGAATGT-5'
R1-6: sense primer(SEQ ID NO: 65):
5'-ATACATATGCGGAAACGCAAGCCTGTAGCCCAT-3' anti-sense primer(SEQ ID NO: 11):
3'-CCCTAGTAACGGGACACTATTTTCGAATGT-5'

Construction of mutein plasmids pT7-TNFM1 and M2

A DNA having a nucleotide sequence encoding TNFM1 mutein was prepared by carrying out PCR using the TNF DNA2 as a template and primers containing the nucleotide sequences to be mutated. The mutant primers are as follows:
M1: sense primer(SEQ ID NO: 66):
5'-GCACATATGCCGAGTGACAAGCCTGTA-3' anti-sense primer(SEQ ID NO: 67):
3'-TGAAACCCTAGTAACGGGACACTATTTTCGAA TGT-5'

The resultant PCR product was digested with the restriction endonucleases NdeI and HindIII to prepare DNA fragment with the restriction sites at each end. Then, the TNFM1 mutein DNA fragment was ligated to the linear pT7-TNF plasmid prepared by digesting with the restriction endonucleases of NdeI and HindIII by using T4 DNA ligase.

By the same procedure as described above, the plasmid pT7-TNFM2 containing a DNA fragment encoding the TNFM2 mutein was prepared. The mutant primers are as follows.

M2: sense primer(SEQ ID NO: 68):
5'-ATACATATGCGGAAACGCAAGCCTGTAGCCCA-3'
anti-sense primer(SEQ ID NO: 69):
3'-TGAAACCCTAGTAACGGAAGACTATTTTCGA
ATGT-5'

Construction of a pT7-TNFM3 mutein plasmid

A DNA fragment having a nucleotide sequence encoding the TNFM3 mutein was prepared by carrying out the procedure as discribed in step 1 of Example(2-A), except that the TNF DNA2 was used as a template and the following M3 primers and the P2 primers were used in place of the R2-1 and the P1 primers, respectively.

M3: sense primer(SEQ ID NO: 70):
5'-GTGGTGCCAATAGAGGGCCTGTTCCTCATCTA
C-3' anti-sense primer(SEQ ID NO: 71):
3'-CACCACGGTTATCTCCCGGACAAGGAGTAGA
TG-5'

P2: sense primer(SEQ ID NO: 72):
5'-ATACATATGCCGAGTGACAAGCCTGTA-3' anti-sense primer(SEQ ID NO: 67):
3'-TGAAACCCTAGTAACGGGACACTATTTTCGAA
TGT-5'

The resultant PCR product was digested with the restriction endonucleases NdeI and HindIII to prepare a DNA fragment with the restriction sites at each end. Then, the TNFM3 mutein DNA fragment was ligated to the linear pT7-TNF plasmid prepared by digesting with the restriction endonucleases of NdeI and HindIII, by using T4 DNA ligase.

By the same procedure as described above, plasmids containing the DNA fragments encoding the TNFM4, M5 and M6 muteins were prepared with the mutant primers as following:

M4: 1) sense primer(SEQ ID NO: 70):
5'-GTGGTGCCAATAGAGGGCCTGTTCCTCATCT
AC-3' anti-sense primer(SEQ ID NO: 71):
3'-CACCACGGTTATCTCCCGGACAAGGAGTAGA
TG-5'
2) sense primer(SEQ ID NO: 68):
5'-ATACATATGCGGAAACGCAAGCCTGTAGCCCA-3'
anti-sense primer(SEQ ID NO: 69):
3'-TGAAACCCTAGTAACGGAAGACTATTTTCGAAT
GT-5'

M5: 1) sense primer(SEQ ID NO: 70):
5'-GTGGTGCCAATAGAGGGCCTGTTCCTCATCTAC-3'
anti-sense primer(SEQ ID NO: 71):
3'-CACCACGGTTATCTCCCGGACAAGGAGTAGA
TG-5'
2) sense primer(SEQ ID NO: 72):
5'-ATACATATGCCGAGTGACAAGCCTGTA-3' anti-sense primer(SEQ ID NO: 73):
3'-TGAAACCCTAGTAACTGAAGACTATTTTCGAAT
GT-5'

M6: 1) sense primer(SEQ ID NO: 70):
5'-GTGGTGCCAATAGAGGGCCTGTTCCTCATCT
AC-3' anti-sense primer(SEQ ID NO: 71):
3'-CACCACGGTTATCTCCCGGACAAGGAGTAGA
TG-5'
2) sense primer(SEQ ID NO: 68):
5'-ATACATATGCGGAAACGCAAGCCTGTAGCCCA-3'
anti-sense primer(SEQ ID NO: 73):
3'-TGAAACCCTAGTAACTGAAGACTATTTTCGAAT
GT-5'

Construction of pT7-TNFR mutein plasmids

The other plasmids containing DNA fragments encoding the TNFR2 to R5 muteins except the above-mentioned pT7-TNFR1 plasmid were constructed as follows.

A DNA fragment having a nucleotide sequence encoding TNFR2-1 mutein was prepared by carrying out in accordance with the method as described in step 1 of Example (2-A), except that the TNF DNA 2 was used as a template and the following R2-1 primers and the following P3 primers were used in place of the R2-1 and the P1 primers, respectively.

R2-1: sense primer:
5'-AATGCCCTCCTGGCCGATGACGTGGAGCTGA
GA-3' (SEQ. ID. No. 9) anti-sense primer:
3'-TTACGGGAGGACCGGCTACTGCACCTCGAC
TCT-5' (SEQ. ID. No. 10)

P3: sense primer(SEQ ID NO: 8):
5'-GCCATACATATGGTCAGATCATCTTCTCGAAC
C-3' anti-sense primer(SEQ ID NO: 11):
3'-CCCTAGTAACGGGACACTATTTTCGAATGT-5'

The resultant PCR product was digested with the restriction endonucleases NdeI and HindIII to prepare a DNA fragment with the restriction sites at each end. Then, the TNFR2-1 mutein DNA fragment was ligated to the linear pT7-TNF plasmid prepared by digesting with the restriction endonucleases of NdeI and HindIII, by using T4 DNA ligase By the same procedure as described above, plasmids containing the DNA fragments encoding other TNFR2 to R5 muteins were prepared by using the following mutant primers instead of R2-1 primers.

R2-2: sense primer (SEQ. ID. No 12):
5'-CTCCTGGCCAAGAAAGTGGAGCTGAGA-3' anti-sense primer (SEQ. ID. No. 13):
3'-GAGGACCGGTTCTTTCACCTCGACTCT-5'

R2-3: sense primer (SEQ. ID. No. 14):
5'-CTCCTGGCCGTTGTAGTGGAGCTGAGA-3' anti-sense primer (SEQ. ID. No. 15):
3'-GAGGACCGGCAACATCACCTCGACTCT-5'

R2-4: sense primer (SEQ. ID. No. 16):
5'-AATGCCCTCCTGGACAATGGCGTG-3' anti-sense primer (SEQ. ID. No. 17):
3'-TTACGGGAGGACCTGTTACCGCAC-5'

R2-5: sense primer (SEQ. ID. No. 18):
5'-AATGCCCTCCTGGACAATGGCTCCGAGCTGA
GA-3' anti-sense primer (SEQ. ID. No. 19):
3'-TTACGGGAGGACCTGTTACCGAGGCTCGACT
CT-5'

R3-1: sense primer (SEQ. ID. No. 20):
5'-TCAGAGGGCCTGTTCCTCATCTAC-3' anti-sense primer (SEQ. ID. No. 21):
3'-AGTCTCCCGGACAAGGAGTAGATG-5'

R3-2: sense primer (SEQ. ID. No. 22):
5'-TGGTGCCAATAGAGGGCCTGTACCT-3' anti-sense primer (SEQ. ID. No. 23):
3'-ACCACGGTTATCTCCCGGACATGGA-5'

R3-3: sense primer (SEQ. ID. No. 24):
5'-TGGTGCCAGAAGAGGGCCTGTACCT-3' anti-sense primer (SEQ. ID. No. 25):
3'-ACCACGGTCTTCTCCCGGACATGGA-5'

R3-4: sense primer (SEQ. ID. No. 26):
5'-TGGTGGTGCCAAAAAAGGGCCTGTAC-3' anti-sense primer (SEQ. ID. No. 27):
3'-ACCACCACGGTTTTTCCCGGACATG-5'

R3-5: sense primer (SEQ. ID. No. 28):
5'-TGGTGCCATCACTGGGCCTGTTC-3[1] anti-sense primer (SEQ. ID. No. 29):
3'-ACCACGGTAGTGACCCGGACAAG-5'

R3-6: sense primer (SEQ. ID. No. 30):
5'-CCATCAGAGGACCTGTACCTC-3' anti-sense primer (SEQ. ID. No. 31):
3'-GGTAGTCTCCTGGACATGGAG-5'

R3-7: sense primer (SEQ. ID. No. 32):
5'-CCATCAGAGGTCCTGTACCTC-3' anti-sense primer (SEQ. ID. No. 33):
3'-GGTAGTCTCCAGGACATGGAG-5'
R3-8: sense primer (SEQ. ID. No. 34):
5'-TCAGAGGGCCTGGAACTCATCTAC-3' anti-sense primer (SEQ. ID. No. 35):
3'-AGTCTCCCGGACCTTGAGTAGATG-5'
R4-1: sense primer (SEQ. ID. No. 36):
5'-ATCGCCGTCTTGTACCAGACCAAG-3' anti-sense primer (SEQ. ID. No. 37):
3'-TAGCGGCAGAACATGGTCTGGTTC-5'
R4-2: sense primer (SEQ. ID. No. 38):
5'-CGCATCGCCGAGAAAGAACAGACCAAG-3' anti-sense primer (SEQ. ID. No. 39):
3'-GCGTAGCGGCTCTTTCTTGTCTGGTTC-5'
R4-3: sense primer (SEQ. ID. No. 40):
5'-ATCGCCGTCAAATACCAGACCAAG-3' anti-sense primer (SEQ. ID. No. 41):
3'-TAGCGGCAGTTTATGGTCTGGTTC-5'
R4-4: sense primer (SEQ. ID. No. 42):
5'-ATCGCCGTCTCCGAACAGACCAAG-3' anti-sense primer (SEQ. ID. No. 43):
3'-TAGCGGCAGAGGCTTGTCTGGTTC-5'
R4-5: sense primer (SEQ. ID. No. 44):
5'-ATCGCCGTCGAGTACGAGACCAAGGTC-3' anti-sense primer (SEQ. ID. No. 45):
3'-TAGCGGCAGCTCATGCTCTGGTTCCAG-5'
R5-1: sense primer (SEQ. ID. No. 46):
5'-TCCAGCTGGCTGCTGGTGACCGA-3' anti-sense primer (SEQ. ID. No. 47):
3'-AGGTCGACCGACGACCACTGGCT-5'
R5-2: sense primer (SEQ. ID. No. 48): 5'-TCCAGCTGGTTGTTGGTGACCGA-3' anti-sense primer (SEQ. ID. No. 49):
3'-AGGTCGACCAACAACCACTGGCT-5'
R5-3: sense primer (SEQ. ID. No. 50):
5'-TTCCAGCTGAAGAAGGGTGACCGA-3' anti-sense primer (SEQ. ID. No. 51):
3'-AAGGTCGACTTCTTCCCACTGGCT-5'
R5-4: sense primer (SEQ. ID. No. 52):
5'-AGCTGGAGGAGGGTGACCGACT-3' anti-sense primer (SEQ ID. No. 53):
3'-TCGACCTCCTCCCACTGGCTGA-5'
R5-5: sense primer (SEQ. ID. No. 54):
5'-AGCTGGAGAAGGAAGACCGACT-3' anti-sense primer (SEQ. ID. No. 55):
3'-TCGACCTCTTCCTTCTGGCTGA-5'
R5-6: sense primer (SEQ. ID. No. 56):
5'-AGCTGGAGAAGAAGGACCGACT-3' anti-sense primer (SEQ. ID. No. 57):
3'-TCGACCTCTTCTTCCTGGCTGA-5'
R5-7: sense primer (SEQ. ID. No. 58):
5'-AGCTGGAGAAGGTCGACCGACT-3' anti-sense primer (SEQ. ID. No. 59):
3'-TCGACCTCTTCCAGCTGGCTGA-5'

Construction of pT7-TNFR(D7) mutein plasmids pT7-TNFR2-5 plasmid was digested with a restriction endonuclease NdeI and the resultant linear plasmid was digested with a restriction endonuclease HindIII and isolated the DNA fragment encoding TNF R2-5 mutein ("TNFR2-5 DNA"). A DNA fragment having a nucleotide sequence encoding the TNFR2-5(D7) mutein was prepared by carrying out PCR using the TNFR2-5 DNA as a template and primers containing the nucleotide sequences to be mutated. The Ml primers were used for the PCR amplification.
M1: sense primer (SEQ. ID. No. 66):
5'-GCACATATGCCGAGTGACAAGCCTGTA-3' anti-sense primer (SEQ. ID. No. 67):
3'-TGAAACCCTAGTAACGGGACACTATTTTCGAATGT-5'

The resultant PCR product was digested with the restriction endonucleases NdeI and HindIII to prepare a DNA fragment with restriction sites at each end. Then, the TNFR2-5(D7) mutein DNA fragment was ligated to the linear pT7- TNFR2-5 or pT7-TNF plasmid which was prepared by digesting with the restriction endonucleases of NdeI and HindIII, by using T4 DNA ligase.

By the same procedure as described above, plasmids containing the DNA fragments encoding other TNFR(D7) muteins, namely, TNFR3-1(D7), TNFR3-2(D7), TNFR4-3 (D7), TNFR4-4(D7) and TNFR4-5(D7) were prepared by carrying out PCR using TNFR3-1, TNFR3-2, TNFR4-3, TNFR4-4 and TNFR4-5 DNA as a template, respectively. The above primers (M1) were used for PCR amplification.

2-B. Expression and purification of human TNF muteins

E. coli JM10 9(DE3) was transformed with each of the expression plasmids containing a DNA fragment encoding a TNF mutein by the same procedure as described in Example (1-B). Thereafter, ampicillin-resistant colony was selected as in example(1-B) and cultured in 50 ml of LB medium containing ampicillin, and E. coli pellet was obtained by centrifugation.

After the cells were ruptured by ultrasonication, TNF muteins with the size of about 17KD were obtained by purifying by the same procedure as described in Example (1-C). Each amount of TNF muteins was varied in the range of 70 μg to 1 mg, which showed a large deviation depending upon the kind of muteins. The TNF muteins prepared in the Examples are summarized in Table 1 below.

TABLE 1

Human TNF muteins and their mutated amino acid(s)

| | Region-1 | Region-2 | Region-3 | Region-4 | Region-5 | Region-6 |
|---|---|---|---|---|---|---|
| | 10 | 41 | 56 | 88 | 130 | 157 |
| mTNF | VRSSSRTPSD | LANGV | SEGLY | AVSYQ | LEKGD | AL |
| R1-1 | RRTPSD | — | — | — | — | — |
| R1-2 | AHPSD | — | — | — | — | — |
| R1-3 | AHRKR | — | — | — | — | — |
| R1-4 | RKPSD | — | — | — | — | — |
| R1-5 | RRRTPSD | — | — | — | — | — |
| R1-6 | RKR | — | — | — | — | — |
| R2-1 | — | LADDV | — | — | — | — |

TABLE 1-continued

Human TNF muteins and their mutated amino acid(s)

| | Region-1 | Region-2 | Region-3 | Region-4 | Region-5 | Region-6 |
|---|---|---|---|---|---|---|
| R2-2 | — | LAKKV | — | — | — | — |
| R2-3 | — | LAVVV | — | — | — | — |
| R2-4 | — | LDNGV | — | — | — | — |
| R2-5 | — | LDNGS | — | — | — | — |
| R3-1 | — | — | SEGLF | — | — | — |
| R3-2 | — | — | IEGLY | — | — | — |
| R3-3 | — | — | EEGLY | — | — | — |
| R3-4 | — | — | KKGLY | — | — | — |
| R3-5 | — | — | SLGLF | — | — | — |
| R3-6 | — | — | SEDLY | — | — | — |
| R3-7 | — | — | SEVLY | — | — | — |
| R3-8 | — | — | SEGLE | — | — | — |
| R4-1 | — | — | — | AVLYQ | — | — |
| R4-2 | — | — | — | AEKEQ | — | — |
| R4-3 | — | — | — | AVKYQ | — | — |
| R4-4 | — | — | — | AVSEQ | — | — |
| R4-5 | — | — | — | AVEYE | — | — |
| R5-1 | — | — | — | — | LAAGD | — |
| R5-2 | — | — | — | — | LVVGD | — |
| R5-3 | — | — | — | — | LKKGD | — |
| R5-4 | — | — | — | — | LEEGD | — |
| R5-5 | — | — | — | — | LEKED | — |
| R5-6 | — | — | — | — | LEKKD | — |
| R5-7 | — | — | — | — | LEKVD | — |
| M1 | PSD | — | — | — | — | — |
| M2 | RKR | — | — | — | — | AF |
| M3 | PSD | — | IEGLF | — | — | — |
| M4 | RKR | — | IEGLF | — | — | AF |
| M5 | PSD | — | IEGLF | — | — | DF |
| M6 | RKR | — | IEGLF | — | — | DF |
| R2-5(D7) | PSD | LDNGS | — | — | — | — |
| R3-1(D7) | PSD | — | SEGLF | — | — | — |
| R3-2(D7) | PSD | — | IEGLY | — | — | — |
| R4-3(D7) | PSD | — | — | AVKYQ | — | — |
| R4-4(D7) | PSD | — | — | AVSEQ | — | — |
| R4-5(D7) | PSD | — | — | AVEYE | — | — |

2-C. Cytotoxicity test

The cytotoxic activities of the muteins were evaluated on TNF-sensitive murine fibrosarcoma L929 cells (ATCC CCL1) in accordance with the method as mentioned previously. The results are summarized in Table 2.

TABLE 2

Characterization of the purified mature hTNF and its muteins.

| TNF derivatives | No. of A.A. | Specific activity (units/mg) | Relative specificity |
|---|---|---|---|
| mature TNF | 157 | $6.24 \times 10^6$ | 1.00 |
| R1-1 | 153 | $1.06 \times 10^7$ | 1.70 |
| R1-2 | 152 | $1.12 \times 10^7$ | 1.80 |
| R1-3 | 152 | $3.12 \times 10^6$ | 0.50 |
| R1-4 | 152 | $1.87 \times 10^6$ | 0.30 |
| R1-5 | 154 | $6.36 \times 10^7$ | 10.2 |
| R1-6 | 150 | $7.49 \times 10^8$ | 1.20 |
| R2-1 | 157 | $6.24 \times 10^5$ | 0.10 |
| R2-2 | 157 | $3.74 \times 10^5$ | 0.01 |
| R2-3 | 157 | $2.50 \times 10^5$ | 0.40 |
| R2-4 | 157 | $1.87 \times 10^5$ | 0.03 |
| R2-5 | 157 | $3.12 \times 10^5$ | 0.05 |
| R3-1 | 157 | $4.80 \times 10^6$ | 0.77 |
| R3-2 | 157 | $9.98 \times 10^6$ | 1.60 |
| R3-3 | 157 | $5.49 \times 10^6$ | 0.88 |
| R3-4 | 157 | $9.36 \times 10^5$ | 0.15 |
| R3-5 | 157 | $1.06 \times 10^7$ | 1.70 |
| R3-6 | 157 | $7.49 \times 10^6$ | 1.20 |
| R3-7 | 157 | $6.30 \times 10^6$ | 1.01 |
| R3-8 | 157 | $5.80 \times 10^6$ | 0.93 |
| R4-1 | 157 | $6.86 \times 10^6$ | 1.10 |
| R4-2 | 157 | $8.10 \times 10^6$ | 1.30 |
| R4-3 | 157 | $1.56 \times 10^7$ | 2.50 |
| R4-4 | 157 | $2.25 \times 10^7$ | 3.60 |
| R4-5 | 157 | $1.62 \times 10^7$ | 2.60 |
| R5-1 | 157 | $4.56 \times 10^6$ | 0.73 |
| R5-2 | 157 | $4.99 \times 10^6$ | 0.80 |
| R5-3 | 157 | $2.81 \times 10^6$ | 0.45 |
| R5-4 | 157 | $7.68 \times 10^6$ | 1.23 |
| R5-5 | 157 | $6.86 \times 10^6$ | 1.10 |
| R5-6 | 157 | $3.99 \times 10^6$ | 0.64 |
| R5-7 | 157 | $3.74 \times 10^4$ | 0.01 |
| M1 | 150 | $7.49 \times 10^6$ | 1.20 |
| M2 | 150 | $5.24 \times 10^7$ | 8.40 |
| M3 | 150 | $1.85 \times 10^8$ | 29.7 |
| M4 | 150 | $2.50 \times 10^7$ | 4.00 |
| M5 | 150 | $7.99 \times 10^7$ | 12.8 |
| M6 | 150 | $6.86 \times 10^6$ | 1.10 |
| R2-5(D7) | 150 | $1.19 \times 10^7$ | 1.90 |
| R3-1(D7) | 150 | $1.72 \times 10^7$ | 2.75 |
| R3-2(D7) | 150 | $1.86 \times 10^7$ | 2.98 |
| R4-3(D7) | 150 | $5.30 \times 10^7$ | 8.50 |
| R4-4(D7) | 150 | $5.80 \times 10^7$ | 9.30 |
| R4-5(D7) | 150 | $5.24 \times 10^7$ | 8.40 |

2-D. Acute lethal toxicity

Female ICR mice were obtained from Myungjin (Seoul, Korea). Eight weeks-old mice with an average body weight of 33 g were used for the lethality tests. Several doses of wild-type TNF or TNF muteins in 500 μl of saline containing 30 mg of D-galactosamine were administered intraperitoneally (i.p.).

Lethality was checked at 24 hr after the administration of TNF or TNF muteins, and lethal toxicity was expressed as the 50% lethal dose (LD50).

TABLE 3

Acute lethal toxicity of wild-type TNF and selected muteins in D-galactosamine-sensitized ICR mice

| TNFs | LD50 (μg/kg) |
|---|---|
| wild-type TNF | 12 |
| M2 | 85 |
| M3 | 3 |
| M4 | 30 |
| M5 | 5 |

TABLE 3-continued

Acute lethal toxicity of wild-type TNF and selected muteins in D-galactosamine-sensitized ICR mice

| TNFs | LD50 (μg/kg) |
|---|---|
| M6 | 21 |
| R1-5 | 42 |
| R4-3(D7) | 21 |
| R4-4(D7) | 8 |
| R4-5(D7) | 3 |

What is claimed is:

1. A polypeptide human TNF mutein comprising an amino acid sequence represented by the amino acid sequence of SEQ ID NO: 1 wherein at least one of the following amino acid replacements occurs:

38th Alanine by Aspartic acid;
    39th Asparagine by Valine;
    40th Glycine by Aspartic acid, Lysine or Valine;
    41st Valine by Serine;
    52nd Serine by Isoleucine;
    53rd Glutamic acid by Lysine or Leucine;
    54th Glycine by Aspartic acid;
    56th Tyrosine by Glutamic acid or Phenyalanine;
    85th Valine by Glutamic acid or Arginine;
    86th Serine by Lysine, Glutamic acid or Aspartic acid;
    87th Tyrosine by Glutamic acid or Arginine;
    88th Glutamine by Glutamic acid;
    127th Glutamic acid by Alanine, Valine or Lysine;
    128th Lysine by Alanine, Valine, or Glutamic acid;
    129th Glycine by Glutamic acid, Lysine or Valine; and
    156th Alanine by Aspartic acid.

2. The polypeptide according to claim 1 wherein the 7 successive amino acids from the N-terminus are further deleted.

3. The polypeptide according to claim 2 wherein the 52nd Serine is replaced by Isoleucine and the 56th Tyrosine is further replaced by Phenylalanine.

4. The polypeptide according to claim 2 wherein the 52nd serine and the 156th Alanine are replaced by Isoleucine and Aspartic acid, respectively; and the 56th Tyrosine ane the 157th Leucine are further replaced by Phenylalanines, respectively.

5. The polypeptide according to claim 2 wherein the 86th Serine is replaced by Lysine.

6. The polypeptide according to claim 2 wherein the 87th Tyrosine is replaced by Glutamic acid.

7. The polypeptide according to claim 2 wherein each of the 86th Serine and the 88th Glutamine is replaced by Glutamic acid.

8. The polypeptide according to claim 1 wherein Methionine is attached to the N-terminus of the amino acid sequence.

9. A pharmaceutical composition comprising a polypeptide according to claim 1 or a pharmaceutically acceptable salt thereof as an active ingredient.

* * * * *

SEQUENCE LISTING ( 1 ) GENERAL INFORMATION:

( i i i ) NUMBER OF SEQUENCES: 73

( 2 ) INFORMATION FOR SEQ ID NO:1:

( i ) SEQUENCE CHARACTERISTICS:
        ( A ) LENGTH: 157 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 1:

```
Val  Arg  Ser  Ser  Ser  Arg  Thr  Pro  Ser  Asp  Lys  Pro  Val  Ala  His
                    5                        10                           15

Val  Val  Ala  Asn  Pro  Gln  Ala  Glu  Gly  Gln  Leu  Gln  Trp  Leu  Asn
                    20                       25                           30

Arg  Arg  Ala  Asn  Ala  Leu  Leu  Ala  Asn  Gly  Val  Glu  Leu  Arg  Asp
                    35                       40                           45

Asn  Gln  Leu  Val  Val  Pro  Ser  Glu  Gly  Leu  Tyr  Leu  Ile  Tyr  Ser
                    50                       55                           60

Gln  Val  Leu  Phe  Lys  Gly  Gln  Gly  Cys  Pro  Ser  Thr  His  Val  Leu
                    65                       70                           75

Leu  Thr  His  Thr  Ile  Ser  Arg  Ile  Ala  Val  Ser  Tyr  Gln  Thr  Lys
                    80                       85                           90

Val  Asn  Leu  Leu  Ser  Ala  Ile  Lys  Ser  Pro  Cys  Gln  Arg  Glu  Thr
                    95                       100                          105

Pro  Glu  Gly  Ala  Glu  Ala  Lys  Pro  Trp  Tyr  Glu  Pro  Ile  Tyr  Leu
                    110                      115                          120

Gly  Gly  Val  Phe  Gln  Leu  Glu  Lys  Gly  Asp  Arg  Leu  Ser  Ala  Glu
                    125                      130                          135

Ile  Asn  Arg  Pro  Asp  Tyr  Leu  Asp  Phe  Ala  Glu  Ser  Gly  Gln  Val
                    140                      145                          150
```

```
Tyr  Phe  Gly  Ile  Ile  Ala  Leu
               155
```

( 2 ) INFORMATION FOR SEQ ID NO: 2:

( i ) SEQUENCE CHARACTERISTICS:
        ( A ) LENGTH: 471 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO: 2:

```
GTC  AGA  TCA  TCT  TCT  CGA  ACC  CCG  AGT  GAC            30
Val  Arg  Ser  Ser  Ser  Arg  Thr  Pro  Ser  Asp
                    5                              10

AAG  CCT  GTA  GCC  CAT  GTT  GTA  GCA  AAC  CCT            60
Lys  Pro  Val  Ala  His  Val  Val  Ala  Asn  Pro
                    15                             20

CAA  GCT  GAG  GGG  CAG  CTC  CAG  TGG  CTG  AAC            90
Gln  Ala  Glu  Gly  Gln  Leu  Gln  Trp  Leu  Asn
                    25                             30

CGC  CGG  GCC  AAT  GCC  CTC  CTG  GCC  AAT  GGC           120
Arg  Arg  Ala  Asn  Ala  Leu  Leu  Ala  Asn  Gly
                    35                             40

GTG  GAG  CTG  AGA  GAT  AAC  CAG  CTG  GTG  GTG           150
Val  Glu  Leu  Arg  Asp  Asn  Gln  Leu  Val  Val
                    45                             50

CCA  TCA  GAG  GGC  CTG  TAC  CTC  ATC  TAC  TCC           180
Pro  Ser  Glu  Gly  Leu  Tyr  Leu  Ile  Tyr  Ser
                    55                             60

CAG  GTC  CTC  TTC  AAG  GGC  CAA  GGC  TGC  CCC           210
Gln  Val  Leu  Phe  Lys  Gly  Gln  Gly  Cys  Pro
                    65                             70

TCC  ACC  CAT  GTG  CTC  CTC  ACC  CAC  ACC  ATC           240
Ser  Thr  His  Val  Leu  Leu  Thr  His  Thr  Ile
                    75                             80

AGC  CGC  ATC  GCC  GTG  TCC  TAC  CAG  ACC  AAG           270
Ser  Arg  Ile  Ala  Val  Ser  Tyr  Gln  Thr  Lys
                    85                             90

GTC  AAC  CTC  CTC  TCT  GCC  ATC  AAG  AGC  CCC           300
Val  Asn  Leu  Leu  Ser  Ala  Ile  Lys  Ser  Pro
                    95                            100

TGC  CAG  AGG  GAG  ACC  CCA  GAG  GGG  GCT  GAG           330
Cys  Gln  Arg  Glu  Thr  Pro  Glu  Gly  Ala  Glu
                   105                            110

GCC  AAG  CCC  TGG  TAT  GAG  CCC  ATC  TAT  CTG           360
Ala  Lys  Pro  Trp  Tyr  Glu  Pro  Ile  Tyr  Leu
                   115                            120

GGA  GGG  GTC  TTC  CAG  CTG  GAG  AAG  GGT  GAC           390
Gly  Gly  Val  Phe  Gln  Leu  Glu  Lys  Gly  Asp
                   125                            130

CGA  CTC  AGC  GCT  GAG  ATC  AAT  CGG  CCC  GAC           420
Arg  Leu  Ser  Ala  Glu  Ile  Asn  Arg  Pro  Asp
                   135                            140

TAT  CTC  GAC  TTT  GCC  GAG  TCT  GGG  CAG  GTC           450
Tyr  Leu  Asp  Phe  Ala  Glu  Ser  Gly  Gln  Val
                   145                            150

TAC  TTT  GGG  ATC  ATT  GCC  CTG                          471
Tyr  Phe  Gly  Ile  Ile  Ala  Leu
                   155
```

( 2 ) INFORMATION FOR SEQ ID NO: 3:

( i ) SEQUENCE CHARACTERISTICS:
        ( A ) LENGTH: 29 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 3:

```
GCACCATGGT CAGATCATCT TCTCGAACC                                              29
```

( 2 ) INFORMATION FOR SEQ ID NO: 4:

( i ) SEQUENCE CHARACTERISTICS:
        ( A ) LENGTH: 35 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 4:

```
TGAAACCCTA GTAACGGGAC ACTATTCCTA GGTGT                                       35
```

( 2 ) INFORMATION FOR SEQ ID NO: 5:

( i ) SEQUENCE CHARACTERISTICS:
        ( A ) LENGTH: 109 bases
        ( B ) TYPE: nucleic acid
        ( C ) STRANDEDNESS: single
        ( D ) TOPOLOGY: linear ( i i ) MOLECULE TYPE: T7 promoter region DNA ( x i ) SEQUENCE DESCRIPTION: SEQ ID NO: 5:

```
GCACCATGGT ATATCTCCTT CTTAAAGTTA AACAAAATTA TTTCTAGAGG                       50
GAAACCGTTG TGGTCTCCCT ATAGTGAGTC GTATTAATTT CGCGGGATCG                      100
AGATCTCCC                                                                  109
```

( 2 ) INFORMATION FOR SEQ ID NO: 6:

( i ) SEQUENCE CHARACTERISTICS:
        ( A ) LENGTH: 27 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 6:

```
GCACCATGGT ATATCTCCTT CTTAAAG                                                27
```

( 2 ) INFORMATION FOR SEQ ID NO: 7:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 7:

```
AAAGCGCCCT AGCTCTAGAG GG                                                     22
```

( 2 ) INFORMATION FOR SEQ ID NO: 8:

( i ) SEQUENCE CHARACTERISTICS:
        ( A ) LENGTH: 33 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 8:

GCCATACATA TGGTCAGATC ATCTTCTCGA ACC        33

( 2 ) INFORMATION FOR SEQ ID NO: 9:

( i ) SEQUENCE CHARACTERISTICS:
        ( A ) LENGTH: 33 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 9:

AATGCCCTCC TGGCCGATGA CGTGGAGCTG AGA        33

( 2 ) INFORMATION FOR SEQ ID NO: 10:

( i ) SEQUENCE CHARACTERISTICS:
        ( A ) LENGTH: 33 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 10:

TTACGGGAGG ACCGGCTACT GCACCTCGAC TCT        33

( 2 ) INFORMATION FOR SEQ ID NO: 11:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 11:

CCCTAGTAAC GGGACACTAT TTTCGAATGT        30

( 2 ) INFORMATION FOR SEQ ID NO: 12:

( i ) SEQUENCE CHARACTERISTICS:
        ( A ) LENGTH: 27 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 12:

CTCCTGGCCA AGAAAGTGGA GCTGAGA        27

( 2 ) INFORMATION FOR SEQ ID NO: 13:

( i ) SEQUENCE CHARACTERISTICS:
        ( A ) LENGTH: 27 bases (B) TYPE: nucleic acid
(C) STRANDEDNESS: single
(D) TOPOLOGY: linear (ii) MOLECULE TYPE: primer DNA (xi) SEQUENCE DESCRIPTION: SEQ ID NO: 13:

GAGGACCGGT TCTTTCACCT CGACTCT 27

(2) INFORMATION FOR SEQ ID NO: 14:

(i) SEQUENCE CHARACTERISTICS:
(A) LENGTH: 27 bases
(B) TYPE: nucleic acid
(C) STRANDEDNESS: single
(D) TOPOLOGY: linear (ii) MOLECULE TYPE: primer DNA (xi) SEQUENCE DESCRIPTION: SEQ ID NO: 14:

CTCCTGGCCG TTGTAGTGGA GCTGAGA 27

(2) INFORMATION FOR SEQ ID NO: 15:

(i) SEQUENCE CHARACTERISTICS:
(A) LENGTH: 27 bases
(B) TYPE: nucleic acid
(C) STRANDEDNESS: single
(D) TOPOLOGY: linear (ii) MOLECULE TYPE: primer DNA (xi) SEQUENCE DESCRIPTION: SEQ ID NO: 15:

GAGGACCGGC AACATCACCT CGACTCT 27

(2) INFORMATION FOR SEQ ID NO: 16:

(i) SEQUENCE CHARACTERISTICS:
(A) LENGTH: 24 bases
(B) TYPE: nucleic acid
(C) STRANDEDNESS: single
(D) TOPOLOGY: linear (ii) MOLECULE TYPE: primer DNA (xi) SEQUENCE DESCRIPTION: SEQ ID NO: 16:

AATGCCCTCC TGGACAATGG CGTG 24

(2) INFORMATION FOR SEQ ID NO: 17:

(i) SEQUENCE CHARACTERISTICS:
(A) LENGTH: 24 bases
(B) TYPE: nucleic acid
(C) STRANDEDNESS: single
(D) TOPOLOGY: linear (ii) MOLECULE TYPE: primer DNA (xi) SEQUENCE DESCRIPTION: SEQ ID NO: 17:

TTACGGGAGG ACCTGTTACC GCAC 24

(2) INFORMATION FOR SEQ ID NO: 18:

(i) SEQUENCE CHARACTERISTICS:
(A) LENGTH: 33 bases
(B) TYPE: nucleic acid
(C) STRANDEDNESS: single
(D) TOPOLOGY: linear (ii) MOLECULE TYPE: primer DNA ( x i ) SEQUENCE DESCRIPTION: SEQ ID NO: 18:

AATGCCCTCC TGGACAATGG CTCCGAGCTG AGA 33

( 2 ) INFORMATION FOR SEQ ID NO: 19:

( i ) SEQUENCE CHARACTERISTICS:
  ( A ) LENGTH: 33 bases
  ( B ) TYPE: nucleic acid
  ( C ) STRANDEDNESS: single
  ( D ) TOPOLOGY: linear ( i i ) MOLECULE TYPE: primer DNA ( x i ) SEQUENCE DESCRIPTION: SEQ ID NO: 19:

TTACGGGAGG ACCTGTTACC GAGGCTCGAC TCT 33

( 2 ) INFORMATION FOR SEQ ID NO: 20:

( i ) SEQUENCE CHARACTERISTICS:
  ( A ) LENGTH: 24 bases
  ( B ) TYPE: nucleic acid
  ( C ) STRANDEDNESS: single
  ( D ) TOPOLOGY: linear ( i i ) MOLECULE TYPE: primer DNA ( x i ) SEQUENCE DESCRIPTION: SEQ ID NO: 20:

TCAGAGGGCC TGTTCCTCAT CTAC 24

( 2 ) INFORMATION FOR SEQ ID NO: 21:

( i ) SEQUENCE CHARACTERISTICS:
  ( A ) LENGTH: 24 bases
  ( B ) TYPE: nucleic acid
  ( C ) STRANDEDNESS: single
  ( D ) TOPOLOGY: linear ( i i ) MOLECULE TYPE: primer DNA ( x i ) SEQUENCE DESCRIPTION: SEQ ID NO: 21:

AGTCTCCCGG ACAAGGAGTA GATG 24

( 2 ) INFORMATION FOR SEQ ID NO: 22:

( i ) SEQUENCE CHARACTERISTICS:
  ( A ) LENGTH: 25 bases
  ( B ) TYPE: nucleic acid
  ( C ) STRANDEDNESS: single
  ( D ) TOPOLOGY: linear ( i i ) MOLECULE TYPE: primer DNA ( x i ) SEQUENCE DESCRIPTION: SEQ ID NO: 22:

TGGTGCCAAT AGAGGGCCTG TACCT 25

( 2 ) INFORMATION FOR SEQ ID NO: 23:

( i ) SEQUENCE CHARACTERISTICS:
  ( A ) LENGTH: 25 bases
  ( B ) TYPE: nucleic acid
  ( C ) STRANDEDNESS: single
  ( D ) TOPOLOGY: linear ( i i ) MOLECULE TYPE: primer DNA ( x i ) SEQUENCE DESCRIPTION: SEQ ID NO: 23:

ACCACGGTTA TCTCCCGGAC ATGGA 25

( 2 ) INFORMATION FOR SEQ ID NO: 24:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 24:

TGGTGCCAGA AGAGGGCCTG TACCT    25

( 2 ) INFORMATION FOR SEQ ID NO: 25:

( i ) SEQUENCE CHARACTERISTICS:
        ( A ) LENGTH: 25 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 25:

ACCACGGTCT TCTCCCGGAC ATGGA    25

( 2 ) INFORMATION FOR SEQ ID NO: 26:

( i ) SEQUENCE CHARACTERISTICS:
        ( A ) LENGTH: 26 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 26:

TGGTGGTGCC AAAAAAGGGC CTGTAC    26

( 2 ) INFORMATION FOR SEQ ID NO: 27:

( i ) SEQUENCE CHARACTERISTICS:
        ( A ) LENGTH: 26 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 27:

ACCACCACGG TTTTTTCCCG GACATG    26

( 2 ) INFORMATION FOR SEQ ID NO: 28:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 28:

TGGTGCCATC ACTGGGCTG TTC    23

( 2 ) INFORMATION FOR SEQ ID NO: 29:

( i ) SEQUENCE CHARACTERISTICS:
        ( A ) LENGTH: 23 bases (B) TYPE: nucleic acid
        (C) STRANDEDNESS: single
        (D) TOPOLOGY: linear (ii) MOLECULE TYPE: primer DNA (xi) SEQUENCE DESCRIPTION: SEQ ID NO: 29:

ACCACGGTAG TGACCCGGAC AAG                                            23

(2) INFORMATION FOR SEQ ID NO: 30:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: primer DNA (xi) SEQUENCE DESCRIPTION: SEQ ID NO: 30:

CCATCAGAGG ACCTGTACCT C                                              21

(2) INFORMATION FOR SEQ ID NO: 31:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: primer DNA (xi) SEQUENCE DESCRIPTION: SEQ ID NO: 31:

GGTAGTCTCC TGGACATGGA G                                              21

(2) INFORMATION FOR SEQ ID NO: 32:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: primer DNA (xi) SEQUENCE DESCRIPTION: SEQ ID NO: 32:

CCATCAGAGG TCCTGTACCT C                                              21

(2) INFORMATION FOR SEQ ID NO: 33:

(i) SEQUENCE CHARACTERISTICS:
        (A) LENGTH: 21 bases
        (B) TYPE: nucleic acid
        (C) STRANDEDNESS: single
        (D) TOPOLOGY: linear (ii) MOLECULE TYPE: primer DNA (xi) SEQUENCE DESCRIPTION: SEQ ID NO: 33:

GGTAGTCTCC AGGACATGGA G                                              21

(2) INFORMATION FOR SEQ ID NO: 34:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: primer DNA ( x i ) SEQUENCE DESCRIPTION: SEQ ID NO: 34:

TCAGAGGGCC TGGAACTCAT CTAC 24

( 2 ) INFORMATION FOR SEQ ID NO: 35:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 35:

AGTCTCCCGG ACCTTGAGTA GATG 24

( 2 ) INFORMATION FOR SEQ ID NO: 36:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 36:

ATCGCCGTCT TGTACCAGAC CAAG 24

( 2 ) INFORMATION FOR SEQ ID NO: 37:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 37:

TAGCGGCAGA ACATGGTCTG GTTC 24

( 2 ) INFORMATION FOR SEQ ID NO: 38:

( i ) SEQUENCE CHARACTERISTICS:
        ( A ) LENGTH: 27 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 38:

CGCATCGCCG AGAAAGAACA GACCAAG 27

( 2 ) INFORMATION FOR SEQ ID NO: 39:

( i ) SEQUENCE CHARACTERISTICS:
        ( A ) LENGTH: 27 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 39:

GCGTAGCGGC TCTTTCTTGT CTGGTTC 27

(2) INFORMATION FOR SEQ ID NO: 40:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: primer DNA (xi) SEQUENCE DESCRIPTION: SEQ ID NO: 40:

ATCGCCGTCA AATACCAGAC CAAG          24

(2) INFORMATION FOR SEQ ID NO: 41:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: primer DNA (xi) SEQUENCE DESCRIPTION: SEQ ID NO: 41:

TAGCGGCAGT TTATGGTCTG GTTC          24

(2) INFORMATION FOR SEQ ID NO: 42:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: primer DNA (xi) SEQUENCE DESCRIPTION: SEQ ID NO: 42:

ATCGCCGTCT CCGAACAGAC CAAG          24

(2) INFORMATION FOR SEQ ID NO: 43:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: primer DNA (xi) SEQUENCE DESCRIPTION: SEQ ID NO: 43:

TAGCGGCAGA GGCTTGTCTG GTTC          24

(2) INFORMATION FOR SEQ ID NO: 44:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: primer DNA (xi) SEQUENCE DESCRIPTION: SEQ ID NO: 44:

ATCGCCGTCG AGTACGAGAC CAAGGTC          27

(2) INFORMATION FOR SEQ ID NO: 45:

(i) SEQUENCE CHARACTERISTICS:
        (A) LENGTH: 27 bases ( B ) TYPE: nucleic acid
           ( C ) STRANDEDNESS: single
           ( D ) TOPOLOGY: linear ( i i ) MOLECULE TYPE: primer DNA ( x i ) SEQUENCE DESCRIPTION: SEQ ID NO: 45:

TAGCGGCAGC TCATGCTCTG GTTCCAG                                                                27

( 2 ) INFORMATION FOR SEQ ID NO: 46:

( i ) SEQUENCE CHARACTERISTICS:
           ( A ) LENGTH: 23 bases
           ( B ) TYPE: nucleic acid
           ( C ) STRANDEDNESS: single
           ( D ) TOPOLOGY: linear ( i i ) MOLECULE TYPE: primer DNA ( x i ) SEQUENCE DESCRIPTION: SEQ ID NO: 46:

TCCAGCTGGC TGCTGGTGAC CGA                                                                    23

( 2 ) INFORMATION FOR SEQ ID NO: 47:

( i ) SEQUENCE CHARACTERISTICS:
           ( A ) LENGTH: 23 bases
           ( B ) TYPE: nucleic acid
           ( C ) STRANDEDNESS: single
           ( D ) TOPOLOGY: linear ( i i ) MOLECULE TYPE: primer DNA ( x i ) SEQUENCE DESCRIPTION: SEQ ID NO: 47:

AGGTCGACCG ACGACCACTG GCT                                                                    23

( 2 ) INFORMATION FOR SEQ ID NO: 48:

( i ) SEQUENCE CHARACTERISTICS:
           ( A ) LENGTH: 23 bases
           ( B ) TYPE: nucleic acid
           ( C ) STRANDEDNESS: single
           ( D ) TOPOLOGY: linear ( i i ) MOLECULE TYPE: primer DNA ( x i ) SEQUENCE DESCRIPTION: SEQ ID NO: 48:

TCCAGCTGGT TGTTGGTGAC CGA                                                                    23

( 2 ) INFORMATION FOR SEQ ID NO: 49:

( i ) SEQUENCE CHARACTERISTICS:
           ( A ) LENGTH: 23 bases
           ( B ) TYPE: nucleic acid
           ( C ) STRANDEDNESS: single
           ( D ) TOPOLOGY: linear ( i i ) MOLECULE TYPE: primer DNA ( x i ) SEQUENCE DESCRIPTION: SEQ ID NO: 49:

AGGTCGACCA ACAACCACTG GCT                                                                    23

( 2 ) INFORMATION FOR SEQ ID NO: 50:

( i ) SEQUENCE CHARACTERISTICS:
           ( A ) LENGTH: 24 bases
           ( B ) TYPE: nucleic acid
           ( C ) STRANDEDNESS: single
           ( D ) TOPOLOGY: linear ( i i ) MOLECULE TYPE: primer DNA ( x i ) SEQUENCE DESCRIPTION: SEQ ID NO: 50:

TTCCAGCTGA AGAAGGGTGA CCGA 24

( 2 ) INFORMATION FOR SEQ ID NO: 51:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 51:

AAGGTCGACT TCTTCCCACT GGCT 24

( 2 ) INFORMATION FOR SEQ ID NO: 52:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 52:

AGCTGGAGGA GGGTGACCGA CT 22

( 2 ) INFORMATION FOR SEQ ID NO: 53:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 53:

TCGACCTCCT CCCACTGGCT GA 22

( 2 ) INFORMATION FOR SEQ ID NO: 54:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 54:

AGCTGGAGAA GGAAGACCGA CT 22

( 2 ) INFORMATION FOR SEQ ID NO: 55:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 55:

TCGACCTCTT CCTTCTGGCT GA 22

( 2 ) INFORMATION FOR SEQ ID NO: 56:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 56:

AGCTGGAGAA GAAGGACCGA CT      22

( 2 ) INFORMATION FOR SEQ ID NO: 57:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 57:

TCGACCTCTT CTTCCTGGCT GA      22

( 2 ) INFORMATION FOR SEQ ID NO:58:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 58:

AGCTGGAGAA GGTCGACCGA CT      22

( 2 ) INFORMATION FOR SEQ ID NO: 59:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 59:

TCGACCTCTT CCAGCTGGCT GA      22

( 2 ) INFORMATION FOR SEQ ID NO: 60:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( i i ) MOLECULE TYPE: primer DNA ( x i ) SEQUENCE DESCRIPTION: SEQ ID NO: 60:

TATCATATGC GTCGAACCCC GAGTGACAAG      30

( 2 ) INFORMATION FOR SEQ ID NO: 61:

( i ) SEQUENCE CHARACTERISTICS:
        ( A ) LENGTH: 31 bases (B) TYPE: nucleic acid
(C) STRANDEDNESS: single
(D) TOPOLOGY: linear (ii) MOLECULE TYPE: primer DNA (xi) SEQUENCE DESCRIPTION: SEQ ID NO: 61:

TATCATATGG CTCATCCGAG TGACAAGCCT G          31

(2) INFORMATION FOR SEQ ID NO: 62:

(i) SEQUENCE CHARACTERISTICS:
(A) LENGTH: 33 bases
(B) TYPE: nucleic acid
(C) STRANDEDNESS: single
(D) TOPOLOGY: linear (ii) MOLECULE TYPE: primer DNA (xi) SEQUENCE DESCRIPTION: SEQ ID NO: 62:

TATCATATGG CTCACCGGAA ACGCAAGCCT GTA          33

(2) INFORMATION FOR SEQ ID NO: 63:

(i) SEQUENCE CHARACTERISTICS:
(A) LENGTH: 29 bases
(B) TYPE: nucleic acid
(C) STRANDEDNESS: single
(D) TOPOLOGY: linear (ii) MOLECULE TYPE: primer DNA (xi) SEQUENCE DESCRIPTION: SEQ ID NO: 63:

CGCCATATGC GAAAACCGAG TGACAAGCC          29

(2) INFORMATION FOR SEQ ID NO: 64:

(i) SEQUENCE CHARACTERISTICS:
(A) LENGTH: 32 bases
(B) TYPE: nucleic acid
(C) STRANDEDNESS: single
(D) TOPOLOGY: linear (ii) MOLECULE TYPE: primer DNA (xi) SEQUENCE DESCRIPTION: SEQ ID NO: 64:

TATCATATGC GTCGTCGAAC CCCGAGTGAC AA          32

(2) INFORMATION FOR SEQ ID NO: 65:

(i) SEQUENCE CHARACTERISTICS:
(A) LENGTH: 33 bases
(B) TYPE: nucleic acid
(C) STRANDEDNESS: single
(D) TOPOLOGY: linear (ii) MOLECULE TYPE: primer DNA (xi) SEQUENCE DESCRIPTION: SEQ ID NO: 65:

ATACATATGC GGAAACGCAA GCCTGTAGCC CAT          33

(2) INFORMATION FOR SEQ ID NO: 66:

(i) SEQUENCE CHARACTERISTICS:
(A) LENGTH: 27 bases
(B) TYPE: nucleic acid
(C) STRANDEDNESS: single
(D) TOPOLOGY: linear (ii) MOLECULE TYPE: primer DNA -continued (x i) SEQUENCE DESCRIPTION: SEQ ID NO: 66:

GCACATATGC CGAGTGACAA GCCTGTA 27

(2) INFORMATION FOR SEQ ID NO: 67:

(i) SEQUENCE CHARACTERISTICS:
        (A) LENGTH: 35 bases
        (B) TYPE: nucleic acid
        (C) STRANDEDNESS: single
        (D) TOPOLOGY: linear (i i) MOLECULE TYPE: primer DNA (x i) SEQUENCE DESCRIPTION: SEQ ID NO: 67:

TGAAACCCTA GTAACGGGAC ACTATTTTCG AATGT 35

(2) INFORMATION FOR SEQ ID NO: 68:

(i) SEQUENCE CHARACTERISTICS:
        (A) LENGTH: 32 bases
        (B) TYPE: nucleic acid
        (C) STRANDEDNESS: single
        (D) TOPOLOGY: linear (i i) MOLECULE TYPE: primer DNA (x i) SEQUENCE DESCRIPTION: SEQ ID NO: 68:

ATACATATGC GGAAACGCAA GCCTGTAGCC CA 32

(2) INFORMATION FOR SEQ ID NO: 69:

(i) SEQUENCE CHARACTERISTICS:
        (A) LENGTH: 35 bases
        (B) TYPE: nucleic acid
        (C) STRANDEDNESS: single
        (D) TOPOLOGY: linear (i i) MOLECULE TYPE: primer DNA (x i) SEQUENCE DESCRIPTION: SEQ ID NO: 69:

TGAAACCCTA GTAACGGAAG ACTATTTTCG AATGT 35

(2) INFORMATION FOR SEQ ID NO: 70:

(i) SEQUENCE CHARACTERISTICS:
        (A) LENGTH: 33 bases
        (B) TYPE: nucleic acid
        (C) STRANDEDNESS: single
        (D) TOPOLOGY: linear (i i) MOLECULE TYPE: primer DNA (x i) SEQUENCE DESCRIPTION: SEQ ID NO: 70:

GTGGTGCCAA TAGAGGGCCT GTTCCTCATC TAC 33

(2) INFORMATION FOR SEQ ID NO: 71:

(i) SEQUENCE CHARACTERISTICS:
        (A) LENGTH: 33 bases
        (B) TYPE: nucleic acid
        (C) STRANDEDNESS: single
        (D) TOPOLOGY: linear (i i) MOLECULE TYPE: primer DNA (x i) SEQUENCE DESCRIPTION: SEQ ID NO: 71:

CACCACGGTT ATCTCCCGGA CAAGGAGTAG ATG 33

(2) INFORMATION FOR SEQ ID NO: 72:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: primer DNA (xi) SEQUENCE DESCRIPTION: SEQ ID NO: 72:

ATACATATGC CGAGTGACAA GCCTGTA        27

(2) INFORMATION FOR SEQ ID NO: 73:

(i) SEQUENCE CHARACTERISTICS:
        (A) LENGTH: 35 bases
        (B) TYPE: nucleic acid
        (C) STRANDEDNESS: single
        (D) TOPOLOGY: linear (ii) MOLECULE TYPE: primer DNA (xi) SEQUENCE DESCRIPTION: SEQ ID NO: 73:

TGAAACCCTA GTAACTGAAG ACTATTTTCG AATGT        35